United States Patent
Edwardson et al.

(10) Patent No.: US 6,818,166 B2
(45) Date of Patent: Nov. 16, 2004

(54) METHOD OF FORMING A FIBER WEB FOR USE IN ABSORBENT PRODUCTS, AND FIBER WEB PRODUCED ACCORDING TO THE METHOD

(75) Inventors: Gunnar Edwardson, Bohus Björkö (SE); Claes Göransson, Landvetter (SE)

(73) Assignee: SCA Hygiene Products AB, Gothenburg (SE)

(*) Notice: Subject to any disclaimer, the term of this patent is extended or adjusted under 35 U.S.C. 154(b) by 92 days.

(21) Appl. No.: 10/125,397

(22) Filed: Apr. 19, 2002

(65) Prior Publication Data

US 2002/0168909 A1 Nov. 14, 2002

Related U.S. Application Data

(60) Provisional application No. 60/284,873, filed on Apr. 20, 2001.

(51) Int. Cl.$^7$ .................................................. B27N 3/04
(52) U.S. Cl. .................... 264/113; 264/119; 264/120; 264/121; 264/145; 264/153; 264/257; 264/258; 264/293; 264/319; 156/196; 156/276
(58) Field of Search ................ 264/112–113, 119–120, 264/145, 153, 257, 258, 293, 121, 319; 156/196, 276

(56) References Cited

U.S. PATENT DOCUMENTS

| | | | |
|---|---|---|---|
| 3,501,813 A | | 3/1970 | Lee et al. |
| 3,518,726 A | | 7/1970 | Banks |
| 3,717,905 A | | 2/1973 | Furbeck |
| 3,871,378 A | * | 3/1975 | Duncan et al. ............. 128/290 |
| 3,956,906 A | * | 5/1976 | Cassidy, Sr. ................ 128/287 |
| 4,016,628 A | | 4/1977 | Kolbach |
| 4,074,959 A | | 2/1978 | Curry et al. |
| 4,268,340 A | * | 5/1981 | Fitzgerald et al. .......... 156/296 |
| 4,388,056 A | | 6/1983 | Lee et al. |
| 4,551,191 A | * | 11/1985 | Kock et al. ................. 156/276 |
| 4,598,441 A | | 7/1986 | Stemmler |
| 4,600,458 A | * | 7/1986 | Kramer et al. ............. 156/199 |
| 4,610,678 A | | 9/1986 | Weisman et al. |
| 4,650,480 A | * | 3/1987 | Stemmler ................... 604/368 |

(List continued on next page.)

FOREIGN PATENT DOCUMENTS

| | | |
|---|---|---|
| DE | 34 13 925 A1 | 10/1985 |
| DE | 43 35 919 A1 | 4/1995 |
| EP | 0 292 624 A1 | 11/1988 |
| EP | 0 336 578 A1 | 10/1989 |
| EP | 0 399 511 A2 | 11/1990 |
| EP | 0 292 624 B1 | 11/1992 |
| FR | 2 388 937 | 11/1978 |
| GB | 1 055 441 | 1/1967 |
| GB | 1 595 905 | 8/1981 |
| GB | 2 124 264 A | 2/1984 |
| WO | 97/19659 | 6/1997 |
| WO | 99/60964 | 12/1999 |
| WO | 01/66345 A1 | 9/2001 |

*Primary Examiner*—Stefan Staicovici
(74) *Attorney, Agent, or Firm*—Burns, Doane, Swecker & Mathis, L.L.P.

(57) ABSTRACT

Method of forming a fiber web (210) intended for use in absorbent products, such as sanitary towels, by air-laying fibers. Separate air flows containing fibers are fed to a number n of different mat-forming wheels (160, 170, 180), where n is a whole number which is at least 2. Separate web layers (161, 171, 181) are formed on each mat-forming wheel. The fiber web (210) is formed by virtue of said web layers being combined downstream of the mat-forming wheels to form a common fiber web which is imparted very great manufacturing accuracy by virtue of the manufacturing method. The manufacturing speed and thus the web speed can be very high, and the desired manufacturing accuracy at the web speed concerned is achieved by selecting a sufficiently great number n of mat-forming wheels. The invention also relates to a fiber web manufactured according to the method.

19 Claims, 5 Drawing Sheets

U.S. PATENT DOCUMENTS

| | | |
|---|---|---|
| 4,761,258 A | 8/1988 | Enloe |
| 4,765,780 A | 8/1988 | Angstadt |
| 4,859,388 A | 8/1989 | Peterson et al. |
| 5,145,351 A | 9/1992 | Rossi |
| 5,916,670 A | 6/1999 | Tan et al. |
| 5,948,507 A * | 9/1999 | Chen et al. .................. 428/153 |
| 5,972,265 A * | 10/1999 | Marra et al. ................. 264/112 |
| 6,048,489 A * | 4/2000 | Reiter et al. ................. 264/510 |
| 2002/0156441 A1 * | 10/2002 | Sawyer et al. .............. 604/368 |

\* cited by examiner

METHOD OF FORMING A FIBER WEB FOR USE IN ABSORBENT PRODUCTS, AND FIBER WEB PRODUCED ACCORDING TO THE METHOD

This application claims priority under 35 U.S.C. § 119 to U.S. Provisional Application No. 60/284,873 entitled METHOD OF FORMING A FIBRE WEB FOR USE IN ABSORBENT PRODUCTS, AND FIBER WEB PRODUCT ACCORDING TO THE METHOD and filed on Apr. 20, 2001, the entire content of which is hereby incorporated by reference.

TECHNICAL FIELD

The present invention relates to a method of forming a web of fibres intended for use in absorbent products, such as sanitary towels, incontinence products, nappies or the like, by air-laying fibres. The invention also relates to a fibre web produced using this method.

BACKGROUND ART

Absorption bodies for use in disposable absorbent products of the type mentioned above are produced from what is known as fluff pulp made from cellulose. Fluff pulp comes in various forms, such as mechanical, thermomechanical, chemithermomechanical or chemical pulp. Fluff pulp is delivered in bales or rolls and is defibrated in mills before forming. The mat formation for forming absorption bodies is carried out by defibrated pulp being transported in an air flow towards a forming wire, usually in the form of what is known as a mat-forming wheel. This is air-permeable and the fibres remain on the periphery of the mat-forming wheel and form a fibre mat of low density, which fibre mat is compressed to the desired density in further processing.

During mat formation, a continuous web of fibre material can be formed, which web is compressed and cut to form individual absorption bodies. In further handling, these can be separated in the web direction for separate positioning between web materials running continuously in the web direction, which are intended to form a covering around separate absorption bodies to form individual products, such as nappies, sanitary towels, incontinence products or the like.

It is also common to combine the individual absorption bodies with a further absorption body of different density and extent. One purpose of having two or more absorption bodies of different density in an absorbent product can be to create a density gradient in the thickness direction of the product in order to control liquid transfer into the product. Another purpose can be that it is desirable to have a highly compressed spreading layer which has the capacity to spread received liquid over the length of the entire product for better utilization of available absorption material. This is because it is a common problem with absorbent products, such as nappies or the like, that the product becomes locally saturated with liquid and leakage occurs long before available absorption material is utilized. When two absorption bodies which are to work together are combined, however, it is necessary for the separate layers to cohere intimately so that an insulating interspace is not formed between the layers, that is to say areas in which the layers are separated and liquid transfer consequently does not take place effectively between the layers. If an insulating interspace is present between the two absorbent layers, the risk of leakage in the lateral direction of the product is of course great. In practice therefore, after two different layers of different density have been combined, it is necessary to compress the layers arranged one on the other. After the two layers of different density have been co-compressed in such a manner, the desired effects mentioned above are lost to a greater or lesser extent.

Mat formation can also be carried out by separate absorption bodies being airlaid in moulds arranged with a uniform mutual spacing over the periphery of the mat-forming wheel. Mat formation can then be effected either by continuous forming taking place on the mat-forming wheel and the fibre material outside the moulds being brushed away and fed back into the system or by the fibre material being guided only into the separate moulds. In the former case, the brushing can interfere with the absorption bodies formed and tear these. This problem is particularly marked if the absorption body formed is not homogeneous but there are irregularities caused by flock formation during forming. In such cases, large chunks or clumps can be torn out of the absorption bodies during brushing, so that the quality becomes variable, even to the extent that large hollows appear in the absorption bodies. When the fibre material is guided only to the moulds, there is a risk of great disruption in the air flow at the edge portions of the moulds, which can cause defects in the absorption bodies.

The development of mat-forming in moulds on mat-forming wheels has been going on for a very long time. As early as in 1970, U.S. Pat. No. 3,518,726 described mat-forming in moulds, where the air flow and the forming in the moulds is controlled by the bottom in the moulds having different hole density and/or different hole size in different areas, as a result of which the absorption bodies formed can have different thickness in different areas and/or different density in different areas. Already in this publication therefore, forming of anatomically adapted absorption bodies for use in, for example, sanitary towels is described.

It has been known for a long time, from inter alia the abovementioned publication, to have moulds with different depth in different areas for forming anatomically adapted absorption bodies. U.S. Pat. No. 4,598,441 deals with the problem that these absorption bodies with different depth in different areas formed in moulds on a mat-forming wheel have the limitation that one side of the absorption body formed is plane and thus not anatomically adapted. U.S. Pat. No. 4,598,441 proposes using two mat-forming wheels, where absorption elements with a profiled side are produced on each mat-forming wheel, after which the plane sides of absorption elements formed on one mat-forming wheel are applied to the plane sides of absorption elements formed on the other mat-forming wheel to create absorption bodies in which the entire outer contour is shaped. In this way therefore, optimally anatomically adapted absorption bodies can be produced.

Over the years, development has moved towards very complicated and large mat-forming wheels. This is due on the one hand to the fact that manufacturing speeds have increased and larger air flows are required for forming the absorption bodies and on the other hand to the fact that it became desirable to have absorption bodies with a number of layers. Mention was made above of the disruptive air flows which can occur in the edge areas of covers which separate the flow of airborne fibres from surrounding air. When a fibre layer is formed on top of a layer already formed in the moulds on a large mat-forming wheel, there is a great risk of disruptive air flows in the edge areas of the covers destroying the layer already formed. EP-B1-0292624, for example, describes a proposal for solving this problem. This document discloses a mat-forming wheel with two mat-forming covers arranged immediately after one another and with two negative-pressure chambers which interact with the covers. For the purpose of avoiding pressure differences at the transition between the two covers, the negative-pressure chamber for one cover extends in under the other cover. A disadvantage of this is that the fibre-forming in one mould is disrupted by the negative pressure from the negative-pressure chamber of an adjacent mould and that as a result the forming becomes uneven. Sealing problems are also described in U.S. Pat. No. 3,717,905.

U.S. Pat. No. 3,501,813 expresses the prejudice that using a number of mat-forming wheels for forming an absorption body with a thicker central part involves considerable disadvantages. This publication states that this procedure with a number of mat-forming wheels it too expensive on the one hand because separate forming units are required for forming each web and on the other hand because equipment is required for combining the webs to form the intended absorption body.

Forming absorption products with a varying basis weight and different thickness in different areas on a single mat-forming wheel is described in a great many patent publications. Examples of these are U.S. Pat. Nos. 4,016,628, 4,388,056, 4,761,258 and 4,859,388. In U.S. Pat. No. 4,761,258, the flow of fibres is controlled by arranging air holes in the forming wire in a selected pattern, in which way the weight per unit area of an absorbent product can be varied in different areas. U.S. Pat. No. 4,859,388 describes the forming of separate absorbent products on a large mat-forming wheel, said products also being compressed in the moulds on the mat-forming wheel. This compression is brought about by a separate, relatively large compression wheel which has a number of radially projecting tooth-like members which are arranged so as, when the two wheels rotate, to penetrate each mould on the mat-forming wheel to compress the absorption bodies formed.

Requirements for increasingly sophisticated absorption bodies in absorbent products, such as sanitary towels, nappies, incontinence products and the like, and efficient high-speed manufacturing have resulted in development moving towards large mat-forming wheels of very complicated construction which take up a great deal of space. The requirement for ever faster manufacturing speed has resulted in the forming length for forming the absorption web becoming increasingly long, which has in turn resulted in the need for larger forming wheels, which require a great deal of energy and, as mentioned above, space. With all the peripheral equipment associated with large mat-forming wheels, factory buildings are often too small, which results in increased investments in the form of building costs when changing over to new, higher-performance mat-forming wheels.

An example of a complicated mat-forming wheel is disclosed in U.S. Pat. No. 4,765,780. In this publication also, the prejudice emerges against using a number of separate mat-forming wheels for the reason that it is too expensive. Instead, a solution is proposed, in which fibres from a common mill are fed in individual fibre flows via separate lines to different forming covers along the periphery of a large mat-forming wheel, different layers being formed on one another as the forming wheel passes the different forming covers. It is stated in U.S. Pat. No. 4,765,780 that this forming installation is particularly suitable in the case of addition of what is known as highly absorbent material. As such highly absorbent material is more expensive than absorbent cellulose fluff pulp fibres, an advantage of the method and the arrangement according to U.S. Pat. No. 4,765,780 is stated to be that the highly absorbent material can be added to one of these fibre flows for positioning within a desired area in the absorption core which is built up on the mat-forming wheel. U.S. Pat. No. 4,765,780 also indicates using a second mat-forming wheel for producing what is known as a take-up zone in the absorbent product, that is to say a zone which is smaller in extent in relation to the length and width of the remaining part of the absorption body. This take-up zone is intended to be arranged directly in front of the genitals of the wearer during use of the product so as to be capable of rapidly taking up large quantities of liquid which are then conveyed onward to the actual absorption body, that is to say the part which is formed from different fibre flows on the first-mentioned mat-forming wheel.

Development is now moving towards increasingly thin absorption bodies, which means greater requirements for manufacturing accuracy in order for the absorbent products to function in the intended manner. Moreover, the demands of consumers for uniform quality and better functioning in terms of leakproofness, fit and comfort are increasingly exacting. Furthermore, requirements for better performance and increased price pressure owing to greater competition result in the manufacturing speed having to be increased considerably.

As mentioned above, increased manufacturing speed results in more exacting requirements in connection with the forming of the absorption web. In combination with demands for considerably thinner products, this results in known manufacturing methods not functioning satisfactorily in all respects.

DISCLOSURE OF INVENTION

The object of the present invention is to produce a manufacturing method which makes higher manufacturing speed possible at the same time as the manufacturing quality increases compared with previously known manufacturing methods.

To this end, the invention is characterized mainly in that separate air flows containing fibres are fed to a number n of different mat-forming wheels, where n is a whole number which is at least 2, in that separate web layers are formed on each mat-forming wheel, in that said intended fibre web is formed by virtue of said web layers being combined downstream of the mat-forming wheels to form a common fibre web which is imparted very great manufacturing accuracy by virtue of the manufacturing method, in that the manufacturing speed and thus the web speed is very high, and in that the desired manufacturing accuracy at the web speed concerned is achieved by selecting a sufficiently great number n of mat-forming wheels.

The manufacturing method according to the invention affords a number of important advantages. The investment costs decrease because small mat-forming wheels are much cheaper than large ones. Furthermore, operating costs are lower because less energy is required to drive a number of small wheels than one large one. The size of the wheels can be reduced by in the order of a factor of 5 if there are, for example, three small mat-forming wheels instead of one large one with the same capacity. The operating costs decrease further as a result of the fact that smaller quantities of air are required in the method according to the present invention compared with forming on a single wheel. When thin layers are formed on small wheels, the pressure drop can be low while, in the case of forming the entire absorption web on a single wheel, a high pressure drop is required in order to mat-form upper layer portions through layers already formed on the mat-forming wheel.

A further advantage of a number of mat-forming wheels arranged one after another is that other materials can be arranged between the web layers and that the method according to the invention is in this way considerably more flexible than conventional manufacturing methods.

The most important advantage of the manufacturing method according to the invention, however, is that the manufacturing accuracy can be increased in spite of increased manufacturing speed compared with mat formation on a single large mat-forming wheel. This is of particular importance when the trend is towards thinner products.

The fibre web is suitably formed by a number n of mat-forming wheels, where n is a whole number which is at least 3. When three mat-forming wheels are used, the manufacturing accuracy is increased by in the order of 50% compared with production on a single mat-forming wheel.

According to a particularly suitable embodiment, the fibre web is compressed in one or more step(s) after forming.

According to one embodiment, the invention is characterized in that at least one air flow has added to it a material in the form of fibres or particles which differs from the material in one or more of the other air flows, in which way a web containing different layers is obtained. The latter embodiment is suitably characterized in that said material in the form of particles or fibres consists of a highly absorbent material, and in that this is added to said air flow together with the first-mentioned fibres. This highly absorbent material in the form of particles or fibres is suitably fed in between at least one pair of adjacent mat-forming wheels by application of said fibres or particles to the web layer formed upstream.

One problem associated with the addition of highly absorbent particles to absorption bodies made of fibre layers is that the particles completely or partly fall through the fibre layer and therefore do not remain in the intended place. In the manufacturing method according to the invention, this can be entirely avoided by virtue of the fact that said web layer formed upstream is compressed before the application of highly absorbent material in the form of fibres or particles.

The method according to the invention is suitably characterized in that the fibre web is compressed to a fibre density of at least 200 kg/m$^3$, preferably between 300 and 700 kg/m$^3$. The method according to the invention is also suitably characterized in that the manufacture of the material web takes place at a speed in excess of 400 m/min. At said manufacturing speeds and degrees of compression, the method according to the invention is superior to previously known manufacturing methods. It is to be pointed out, however, that the production of fibre webs of lower density and/or at lower manufacturing speeds can also take place with greater accuracy using the method according to the present invention compared with conventional techniques.

It is characteristic of the manufacturing method according to the invention that the manufacturing speed of the web can be increased while retaining manufacturing accuracy in terms of variations in weight per unit area in the web formed by adding more mat-forming wheels. The method according to the invention is also characterized in that the manufacturing accuracy in terms of variations in weight per unit area in the web formed can be increased by adding more mat-forming wheels.

The term fibre density means that only fibres forming part of the fibre web are included in the calculation of the density, that is to say additions of, for example, highly absorbent particles to the fibre web do not increase the fibre density.

The method according to the invention is suitably characterized in that the combined fibre web is compressed to a stiffness in the dry state of in the order of 1–15 N measured according to ASTM D 4032-82. The method according to the invention is suitably characterized in that the dry-formed fibre web is, after compression, mechanically softened to the desired hardness. According to a suitable embodiment of the method according to the invention, the invention is characterized in that the dry-formed fibre mat is imparted the desired reduced stiffness and the desired extensibility by virtue of the degree of compression selected and the compression pattern selected.

A fibre web according to the invention for use as absorbent elements in absorbent products, such as sanitary towels, incontinence products, nappies or the like, is characterized mainly in that the fibre web is constructed from a number n of separate web layers, formed one after another on n different mat-forming wheels and combined to form a common fibre web, where n is a whole number which is at least 2, the desired manufacturing accuracy in terms of variation in weight per unit area of the common combined fibre web being achieved by selecting a sufficient number n of web layers formed on n separate mat-forming wheels.

Further suitable embodiments of the method and the fibre web according to the invention emerge from the subsequent patent claims.

BRIEF DESCRIPTION OF DRAWINGS

The invention will be described in greater detail below with reference to embodiments shown in the accompanying drawings, in which:

FIG. 1 illustrates diagrammatically how a fibre web is formed on a large mat-forming wheel 100 according to a previously known manufacturing method. The mat-forming wheel 100 rotates clockwise in the direction of the arrow A. Fibre flows $Q_1$, $Q_2$ and $Q_3$ in the form of a mixture of air and fibres are supplied via separate mat-forming covers 110, 120 and 130 to the forming wire 140 on the mat-forming wheel for construction of the fibre web 150. This is formed as the mat-forming wheel 100 passes each mat-forming cover. Inside the mat-forming wheel 100, negative pressure prevails below the forming wire so that fibres in the fibre air flows adhere to the forming wire while the air travels through the forming wire. A first, lower layer $L_1$ is formed directly in front of the mat-forming cover 110. Above the first, lower layer $L_1$, a second layer $L_2$ of the fibre web is applied directly in front of the mat-forming cover 120, which web is then finished by application of an upper third layer $L_3$ when the fibre web passes the mat-forming cover 130.

A major problem associated with mat-forming the entire fibre web on a single mat-forming wheel is that the forming of the web directly in front of the mat-forming covers 120 and 130 takes place on the previously partly formed web. The air flow directly in front of the mat-forming cover 120 is therefore limited by the layer $L_1$ already applied, and the air flow forming the mat directly in front of the mat-forming cover 130 is limited by the two previously formed layers $L_1$ and $L_2$.

Figure 1:
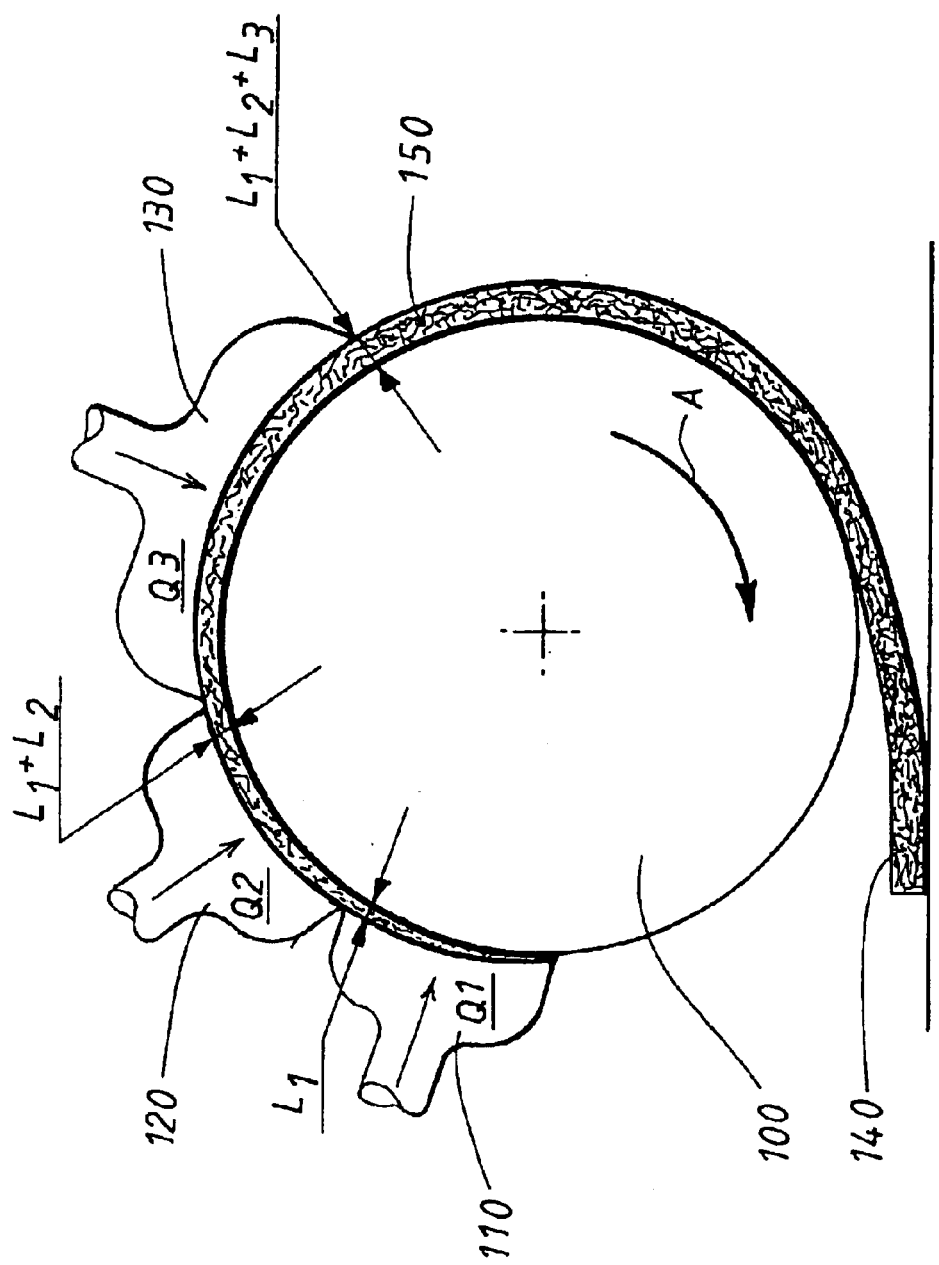
FIG. 1 shows diagrammatically a previously known method of forming a fibre web on a single mat-forming wheel.

In order to compare the mat-forming quality according to the previously known method described in connection with FIG. 1 with the method according to the present invention described below, the following assumptions are made. A fibre web with a combined weight per unit area of 300 g/m² is to be formed on the mat-forming wheel 100, 100 g/m² being applied directly in front of each of the mat-forming covers 110, 120 and 130. At normal negative pressure in the mat-forming wheel, the air speed for forming directly in front of the mat-forming cover 110 can be in the order of 25 m/s. The layer $L_1$ applied under the mat-forming cover 110 limits the air speed for mat-forming directly in front of the second mat-forming cover to in the order of 12 m/s. Correspondingly, the air speed directly in front of the mat-forming cover 130 is limited to in the order of 7 m/s. At lower air speed, but with the same fibre quantity in the air flow, the forming distance directly in front of the mat-forming cover 120 has to be extended in relation to the mat-forming distance directly in front of the mat-forming cover 110, and the mat-forming distance directly in front of the mat-forming cover 130 has to be further extended in a corresponding manner. This in turn means that the mat-forming wheel 100 has to be very large in order to provide the necessary length of forming wire along the periphery of the mat-forming wheel. The size of the mat-forming wheel limits the web speed. If it is desired to increase this, the forming length must be increased if the same mat-forming quality is required, which in turn means that a larger wheel is necessary. In the case of forming in a conventional manner on a single mat-forming wheel, it is therefore not possible to increase the web speed greatly as the latter is limited by the size of the wheel.

If it is assumed that the manufacturing accuracy in forming layers $L_1$, $L_2$ and $L_3$ is 10% for each layer, a variation of 10 g/m² for each layer is obtained, which means that the combined variation is 3×10 g/m², that is to say a total of 30 g/m² or a total of 10%.

Another major problem associated with very large mat-forming wheels is that the size of the wheel sets exacting requirements for the manufacturing accuracy of the wheel. Even small non-roundness deviations on a large wheel result in major problems for mat-laying thin layers on the wheel. The requirements for very great accuracy in the manufacture of large mat-forming wheels results in these being very expensive to manufacture. The manufacturing accuracy requirements also set a practical limit for how large the mat-forming wheels can be made and thus a limit for manufacturing speed.

Figure 2:
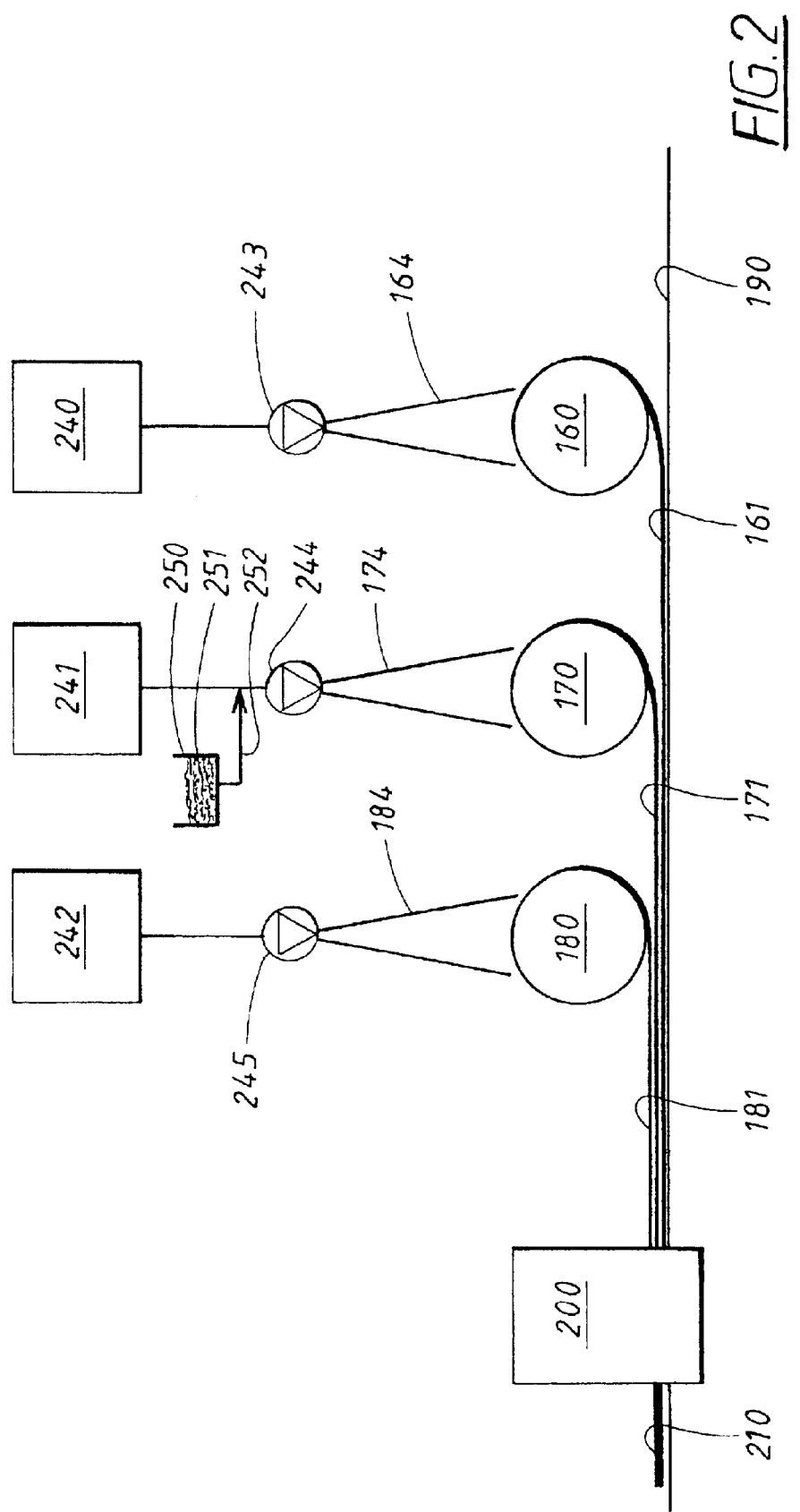
FIG. 2 shows diagrammatically an embodiment of the manufacturing method according to the present invention.

An illustrative embodiment of the method according to the invention is shown in FIG. 2. In the illustrative embodiment shown, an arrangement for implementing the method according to the invention includes three mat-forming wheels 160, 170 and 180 which are small in relation to the mat-forming wheel shown in FIG. 1. On a first mat-forming wheel 160 of said three small mat-forming wheels, a first web layer 161 is formed, which is separated from the mat-forming wheel 160 and conveyed onward on a feeding belt 190. A second web layer 171 is formed on a second mat-forming wheel 170, which second web layer 171 is separated from the mat-forming wheel 170 and laid down on the first web layer for onward transport. Lastly, on a third mat-forming wheel, a third web layer 181 is formed, which is separated from the mat-forming wheel 180 and laid down on the two other web layers 161 and 171 conveyed via the feeding belt 190. The three web layers positioned on one another are fed onward to a compression arrangement 200, where co-compression of the three web layers is carried out in one or more step(s).

In the arrangement according to FIG. 2, mat-forming of the individual web layers takes place continuously on the three mat-forming wheels, as a result of which a single continuous fibre web 210 is formed from the separate web layers. This can, in conjunction with or after compression, be cut into individual absorption bodies, for example in what is known as an RDC cutting wheel (not shown), in which connection individual absorption bodies of any shape can be formed.

The use of a number of small mat-forming wheels for producing separate web layers which are combined to form a common fibre web affords a number of considerable advantages compared with mat-forming on a single large mat-forming wheel. A crucial difference is that, whereas forming on a single large mat-forming wheel has to be seen as forming one single layer, three separate layers are formed when three small mat-forming wheels are used, which layers are subsequently combined. In the example indicated in connection with FIG. 1, a total manufacturing accuracy of 10% is obtained in the manufacture of a fibre web with a weight per unit area of 300 g/m².

In the manufacture of a fibre web with a corresponding weight per unit area using three separate small mat-forming wheels in the manufacturing method according to the invention, the manufacturing accuracy is calculated in a different way. Assume that the standard deviation in production of the layers 161, 171 and 181 is $S_1$, $S_2$ and, respectively, $S_3$. The standard deviation S for the combined fibre web 210 is $$S=\sqrt{S_1^2+S_2^2+S_3^2}$$

If, to illustrate the difference compared with the example described in connection with FIG. 1, it is assumed that a fibre web with a total weight per unit area of 300 g/m² is to be produced by the three small mat-forming moulds 160, 170 and 180 and that a fibre web layer 161, 171 and, respectively, 181 of 100 g/m² is formed by each of said small mat-forming covers with a standard deviation of 10 g/m² for each fibre layer, the total standard deviation for production of the fibre web using the method according to the invention is thus:

$$S_t=\sqrt{10^2+10^2+10^2}$$

$$S_t=17.3 \text{ g/m}^2$$

This is to be compared with 30 g/m² which was the standard deviation for a fibre web with the same total weight per unit area formed on a single mat-forming wheel. By dividing 17.3 by 30, it can be worked out that the standard deviation for a fibre web formed by three small mat-forming wheels is 57% of the standard deviation for a fibre web formed on one large mat-forming wheel. This can also be expressed as the standard deviation having been improved by 43%.

In a corresponding manner, it can be calculated that, if four small mat-forming wheels are used for forming four fibre layers which are then combined to form a common fibre web, the standard deviation is improved by 50% compared with mat-forming a corresponding fibre layer on a single mat-forming wheel.

If only two small mat-forming wheels are used instead of a single large mat-forming wheel, an improvement in the standard deviation of no less than 30% is still obtained.

The method according to the invention is particularly suitable for manufacturing fibre webs at very high speed. In mat-forming on a single mat-forming wheel, a practical capacity ceiling is reached when the size of the forming wheel limits the web speed. In the method according to the present invention, the web speed can be increased without it being necessary to reduce the level of manufacturing accuracy if the number of mat-forming wheels is increased. Furthermore, the manufacturing accuracy in terms of variations in weight per unit area can be increased at the same web speed by increasing the number of mat-forming wheels. With the method according to the invention, it is possible to form even extremely thin fibre webs with great accuracy.

It is quite clearly the trend that consumers of disposable absorbent articles, such as sanitary towels, incontinence products, nappies etc., want increasingly thin products at the same time as they do not wish to forgo function and fit. With the method according to the invention, fibre webs which meet these conditions can be produced. The compression arrangement 200, which is shown only diagrammatically, contains one or more compression unit(s), for example in the form of pairs of rollers between which the fibre web 210 is compressed.

The fibre web is suitably compressed to a stiffness in the dry state of in the order of 1–15 N measured according to ASTM D 4032-82.

If compression in the compression arrangement is very hard, the compressed fibre web is very stiff. This can be compensated if the fibre web is, in connection with the compression step, mechanically softened by compression of the fibre web in a suitable pattern.

Pattern compression can be effected using pattern rollers (not shown). As mentioned above, the compression can take place in one or more step(s), in which connection the pattern compression roller can, for example, constitute the only compression roller or be arranged after a pair of rollers for smooth compression. By virtue of the degree of compression selected and the compression pattern selected, a fibre web formed using the manufacturing method according to the invention can be imparted the desired reduced stiffness and the desired extensibility. Furthermore, the fibre web formed can be compressed with different compression patterns in different areas on those part portions of the fibre mat intended for forming separate absorption cores, as a result of which the separate absorption cores produced have different flexural rigidity in said different areas.

In order for it to be possible to manufacture fibre webs at high speed and with a high degree of compression and also in thin layers, the requirements for manufacturing accuracy are exacting. With the method according to the invention, variation in the weight per unit area can be reduced considerably compared with conventional manufacturing techniques.

A suitable method for determining the variation in weight per unit area on a fibre web is described below.

1. Samples with an area of 1365 mm² are stamped out of the fibre web or the absorption body to be investigated. Samples are taken from different parts of an absorption core, for example the front, the rear, the right side, the left side and the centre, within areas with the same weight per unit area.
2. Measurement is carried out on randomly selected products numbering at least 15, suitably 50.
3. The samples are weighed and standard deviation and mean are calculated. The variation coefficient $C_v$ in per cent is then obtained from:

$$C_v = \frac{S}{\overline{X}} 100$$

4. If it is desired to see the variation in the side or the front/rear, the samples have to be kept in order. This is suitable in order for it to be possible, if necessary, to establish whether there may be a variation of the right/left type.

In the illustrative embodiment shown in FIG. 2, cellulose fluff pulp is fed to each mat-forming wheel 160, 170, 180 in an air flow from mills 240, 241 and, respectively, 242 belonging to the mat-forming wheels, from which fibre is fed by means of blowers 243, 244 and, respectively, 245 in a fibre/air mixture. This is then fed to the mat-forming wheels 160,170 and 180 via mat-forming covers 164, 174, 184 for forming web layers 161,171 and 181 on the respective mat-forming wheels.

If appropriate, at least one air flow with fibres from one of the mills can have added to it a material in the form of particles or fibres which differs from the material in one or more of the other air flows, in which way a web 210 containing different layers is obtained. FIG. 2 shows a container 250 with highly absorbent material in particle form 251, which material can be added via the line 252 to the air flow with fibres which is supplied to the central mat-forming wheel 170, as a result of which a fibre web 210 with highly absorbent material in the central layer is obtained.

Figure 3:
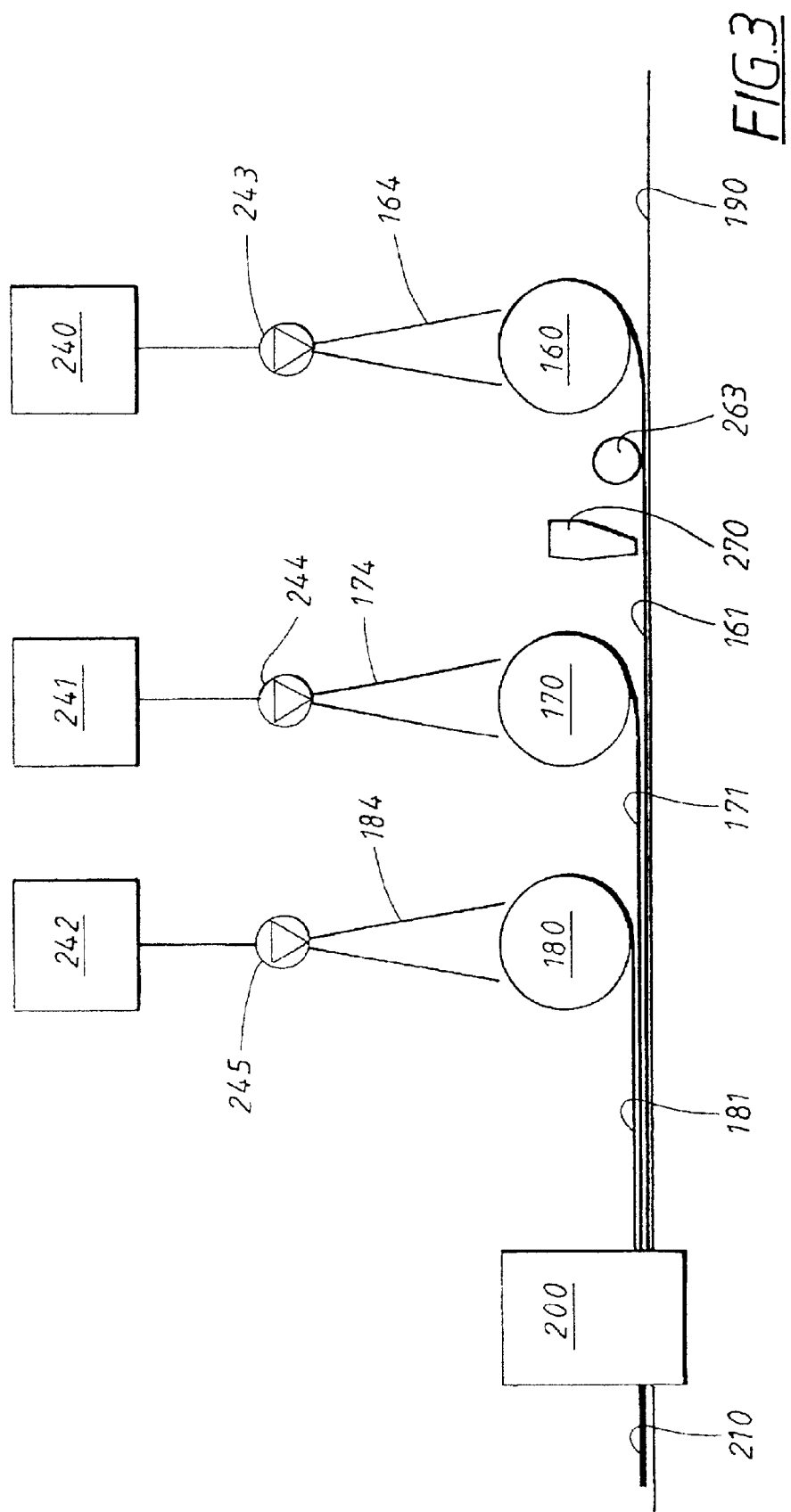
FIG. 3 shows diagrammatically an embodiment of the manufacturing method according to the present invention, modified slightly in relation to the embodiment according to FIG. 2.

FIG. 3 shows an embodiment which is slightly modified in relation to the embodiment according to FIG. 2. In FIG. 3, the components corresponding to similar parts in FIG. 2 have been provided with the same reference numbers.

The embodiment according to FIG. 3 includes a compression roller 263 for compressing the web layer 161 and a device 270 for metering highly absorbent particles for application to the compressed web layer 161. In conventional forming of fibre webs for forming absorption cores for nappies and the like, there have been problems in the addition of highly absorbent particles caused by these particles falling through the fibre web. The method according to the present invention makes possible a simple manner of solving this problem by virtue of, as can be seen from FIG. 3, first compressing one fibre layer to such a density that the particles do not fall through but on the whole remain on the surface. In the subsequent co-compression, the particles are bound firmly in an orderly manner in the fibre web 210.

Figure 4:
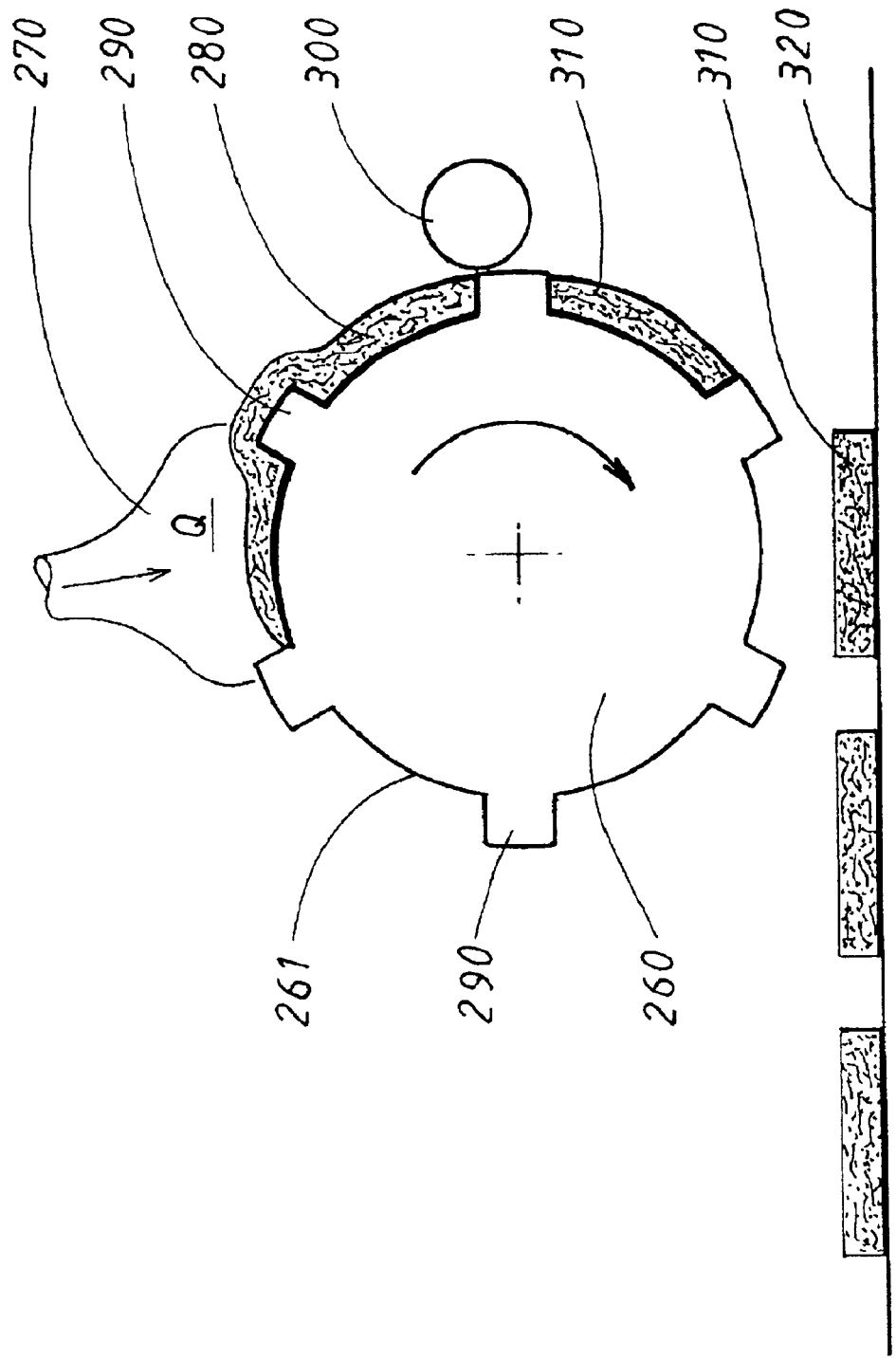
FIG. 4 shows diagrammatically an embodiment for manufacturing separate absorption bodies using the method according to the invention.

For mat-forming at high speed where the requirements for manufacturing accuracy are very exacting, it is suitable for the forming of the fibre web on the mat-forming wheels to take place continuously even though the intention is to produce separate absorption bodies. As mentioned above, any shape of absorption body can be cut out by means of what is known as an RDC cutting wheel after or in conjunction with co-compression of the web layers in the compression arrangement. Alternatively, separate absorption bodies can be produced by continuous mat-forming in the manner illustrated in FIG. 4, which shows diagrammatically a mat-forming wheel 260 with moulds 261 which have the correct size and shape in order to make a part layer of an intended absorption body, for example the absorption core for a sanitary towel or the like. A fibre/air flow Q is supplied continuously via a mat-forming cover 270, and a fibre part layer 280 is formed in a continuous web over the entire mat-forming wheel, that is to say also on the high portions 290 located between the moulds 261. Excess web material formed between the moulds is separated by a milling cutter 300. The separate part layers 310 formed in the moulds 261 are separated from the mat-forming wheel and are conveyed via a conveyor 320 to further small mat-forming wheels (not shown) located downstream of the same type as shown in FIG. 4. Other separate part layers forming part of the intended absorption body are formed on said further mat-forming wheels and are transferred onto the part layers 310 formed upstream. The absorption bodies formed from the different part layers are then compressed in one or more step(s) in a compression arrangement in the same manner as described in connection with the embodiment according to FIG. 2. When separate absorption bodies are formed, as described with reference to FIG. 4, highly absorbent material in the form of fibres or particles, for example, can be added to one or more of the part layers included in conjunction with the forming thereof in the same manner as described in connection with the embodiment according to FIG. 2. Furthermore, by analogy with the embodiment according to FIG. 3, the part layer 310 formed first can be compressed separately, and highly absorbent particles can be applied to the compressed part layer.

An absorbent product which includes an absorption body produced in accordance with the method according to the present invention is described below.

Figure 5:
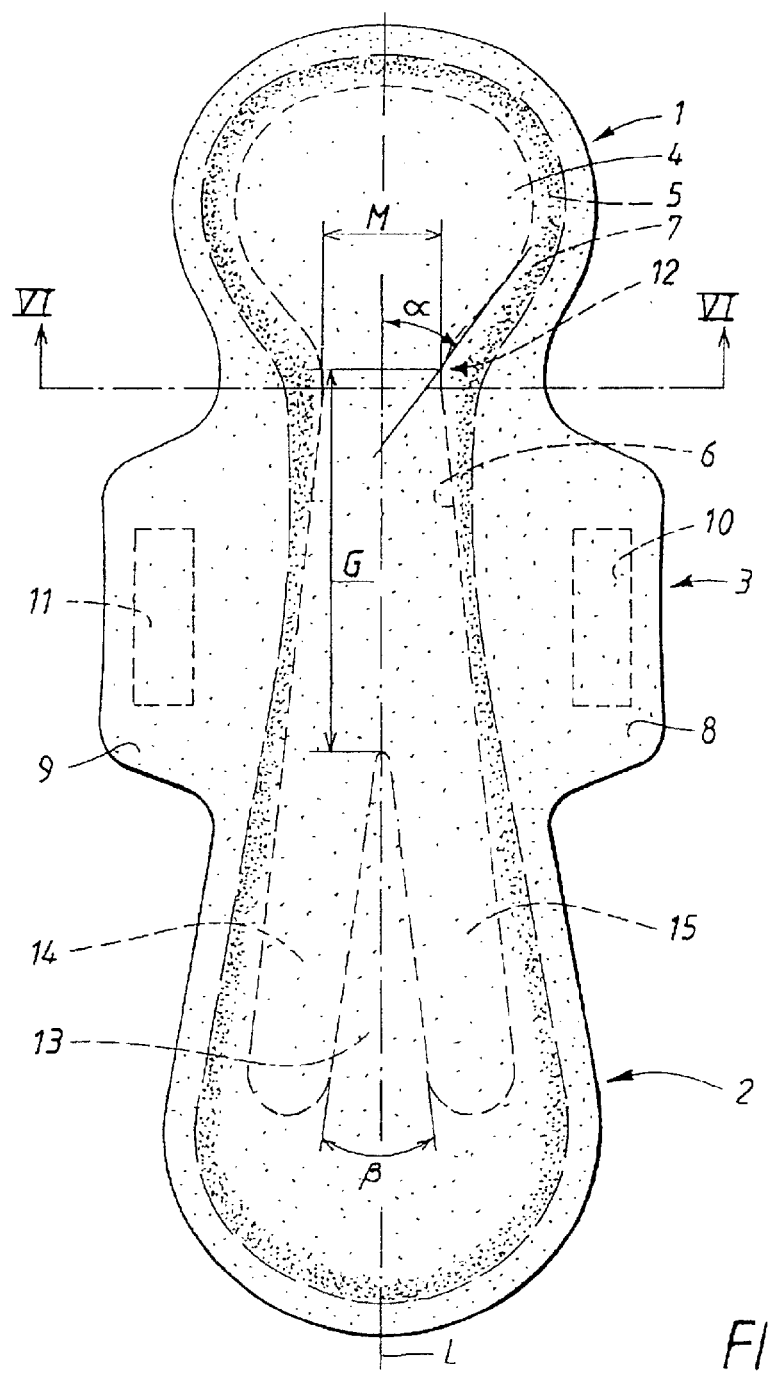
FIG. 5 shows an example of an absorbent product in the form of a sanitary towel or incontinence product with an absorption body made from a fibre web according to the invention.
Figure 6:
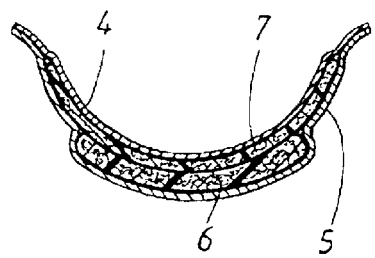
FIG. 6 shows a section along the line VI–VII in FIG. 5 but in a curved utilization state.

FIGS. 5 and 6 show a product in the form of a sanitary towel or incontinence pad. The product is elongate with a longitudinal direction and a transverse direction. The product has a front portion 1, a rear portion 2 and a crotch portion 3 located between said portions. The product shown in FIGS. 5 and 6 comprises a liquid-permeable inner layer 4 which is intended to face the wearer during use of the product. The inner layer, which makes contact directly with the skin of the wearer, is suitably made from a soft, textile-like material. Examples of suitable liquid-permeable materials are various types of what are known as non-woven fabrics. Other examples of suitable materials are perforated plastic films. Net and knitted or woven textiles and combinations and laminates of said materials can also be used as the inner layer. Examples of inner layers for sanitary towels are laminates of different non-wovens and laminates of non-wovens and perforated plastic films. The liquid-permeable layer can also be integrated with underlying drainage or absorption layers, for example a foam plastic with open pores and with a density gradient in the depth direction can serve as a surface layer and as a drainage layer and/or absorption layer.

The absorbent product also has a liquidtight outer layer 5. This usually consists of a thin plastic layer, made of polyethylene for example. It is also possible to use a liquid-permeable material which has been treated with hydrophobing agent in order to make it liquidtight. In particular if the absorbent product is relatively large, it may be suitable for the outer layer to be vapour-permeable in addition to being liquidtight. Such layers can consist of hydrophobed non-woven fabric or of porous plastic films.

The absorbent product includes an absorbent element 6 which is produced using the method according to the present invention and has a keyhole-like shape, and a liquid-permeable insulating layer 7 which likewise has a keyhole-like shape but with a greater extent in both the longitudinal direction and the transverse direction than the absorbent element 6. The outer layer 5 and the inner layer 4 extend with edge portions outside the insulating layer around the latter and are interconnected along these edge portions to form a cover around the absorbent element 6 and the insulating layer 7. In the region of the crotch portion 3, the cover formed by the inner and outer layers extends outwards in the lateral direction to form flexible side flaps 8, 9, what are known as wings, which are intended to be arranged around the crotch portion on the briefs of the wearer in order to protect the edge portions of the briefs from soiling. The wings 8, 9 are suitably provided with adhesive coating, which is indicated in FIG. 1 by reference numbers 10, 11, on the outer layer 5, by means of which the wings can be attached around the legs of the briefs. As can be seen from FIG. 6, the insulating layer 7 is located directly inside the inner layer 4 and is principally intended for rapidly admitting discharged bodily fluid into the underlying absorbent element 6 and forming a liquid-insulating layer so as to reduce what is known as back-wetting from the absorbent element 6 to the inner layer 4 making contact directly with the wearer.

The insulating layer can consist of, for example, an airlaid fibre material of low density bonded together with bonding agent or thermofibre, which is marketed under the designation LDA (low density airlaid). The absorbent element 6 is, seen from the liquid-permeable inner layer 4, arranged under the insulating layer 7. In the product shown, this element is designed to take up and retain essentially all the bodily fluid discharged. The absorbent element 6 has smaller capillaries than the insulating layer 7 located above and therefore draws liquid from the insulating layer and prevents back-wetting by liquid from the absorbent element to the insulating element and to the inner layer 4 which remains essentially dry during use of the product. Only when the absorbent element is saturated with liquid can transport take place from the absorbent element to the insulating layer.

In the illustrative embodiment shown, the absorbent element 6 is also intended to serve as a stiffening element and is for this purpose designed so as to be very stiff in order as far as possible to avoid the absorbent product being compressed in an uncontrolled manner in the event of squeezing forces in the lateral direction generated by the thighs of the wearer in the crotch area. The absorbent stiffening element has a size, shape and stiffness which result in the product, throughout its time of use, retaining a predetermined shape and moreover being retained in the intended position on the wearer. As can be seen from FIG. 1, the absorbent stiffening element 6 extends over the front portion, the entire crotch portion 3 and a considerable part of the rear portion 2.

At the transition 12 between the crotch portion 3 and the front portion 1, the stiffening element 6 has a width M which is adapted to the distance between two particular muscle tendons on both sides of the crotch of the wearer directly in front of the groins. These muscle tendons form part of the muscle group which originates on the inside of the pelvic diaphragm and has its attachment along the thigh. This muscle group consists of the adductor brevis, adductor longus, gracilis and adductor magnus muscles. As mentioned above it is known that this distance between said muscle tendons is very similar for all people. This dimension is in the order of 25–45 mm.

Research has shown that 80% of all women have a dimension of 30–32 mm between said muscle tendons. When said width M essentially corresponds to the distance between said muscle tendons on the wearer, the product will during use be anchored firmly with the transition portion between the muscle tendons and be retained in this position. The two side edges of the front portion diverge in the forward direction on the product from said transition area 12. In this way, the product is prevented from moving backwards between the legs of the wearer. This is a common problem in conventional sanitary towels because the leg movements of the wearer often shift the sanitary towel backwards.

In FIG. 5, an angle between a line in the longitudinal direction of the product and each of said side edges been designated by α. In the case of a large angle α, for example close to 90°, the edges of the front portion may chafe against the groins and legs of the wearer and in this way cause discomfort for the wearer. The smaller the angle α, the greater the risk that the product will slide backwards in between the legs of the wearer. In the case of an angle of less than 30°, this risk is unacceptably high. An angle of 35–45° provides the best balance between secure positioning and comfort. An angle of 45° has been found to be especially favourable.

An absorbent product, such as a sanitary towel, according to the invention is designed with a crotch length adapted to the anatomy of the wearer. In a sanitary towel according to the invention, use has been made of the fact that the great majority of women have a crotch length of in the order of 80–100 mm. The stiffening element 6 has therefore been designed with a corresponding crotch length G of in the order of 70–120 mm, that is to say the distance from the transition area 12 to the start of the rear portion. Along the crotch, where the body shape of the wearer is essentially plane, the sanitary towel according to the invention is designed so as in the dry state to be relatively stiff in the lateral direction, that is to say it is sufficiently stiff not to be deformed in the lateral direction and form creases. As the stiffening element 6 in the embodiment described here also constitutes the major part of the absorption capacity of the sanitary towel, it is essential to be capable of utilizing available space between the legs of the wearer in the crotch. The width of the sanitary towel in the crotch area is, with regard to the stiffening element, limited at the front by said distance between said muscle tendons directly in front of the groins of the wearer. In the backward direction from said transition area to the end of the crotch portion, the width of the stiffening element 6 and thus the absorbent element can increase continuously to in the order of 1.5 times the width in the transition area 12 between the crotch portion and the front portion without any risk of the stiffening element chafing the wearer in the crotch.

The abovementioned geometrical design of the area in and around the transition area 12, that is to say the size of the angle α and the width M, and also the selected crotch length G on the stiffening element for the product according to the invention, affords a very good anatomical adaptation of the stiffening element, which gives the product a good fit and stability of the product in the fitted position on the wearer. This is of particularly great importance for the functioning of the product, not least because the wetting point can, on account of the body position of the genitals of the wearer in the longitudinal direction of the crotch area, vary by as much as in the order of 20 mm for different wearers. As the available space around the wetting point is very limited in width and length, optimum positioning and anchoring in this position of the stiffening absorbent element is necessary. This is achieved by means of said distances M and L selected and said angle a selected.

The anchoring effect is achieved at said muscle tendons even when the width M on the product is less than the distance between said muscle tendons directly in front of the groins. The two edge portions of the front portion diverge in the forward direction, and the product can slide backwards slightly until the edge portions are anchored firmly between said muscle tendons. The distance M on the product is suitably of the order of 15–35 mm and preferably 25–30 mm. The latter distance fits most wearers. If the distance exceeds roughly 35 mm, the product may feel uncomfortable to some wearers. A distance in excess of 45 mm is unsuitable because such products cause discomfort in the form of chafing for most wearers.

The stiffening element 6 and therefore the absorption element also extend some way in over the rear portion 2 of the product. In the rear portion, the stiffening element has a cutout 13 extending from the end edge of the element in the direction of the crotch portion, as a result of which the product can fold along a longitudinal line in the cutout and the parts, the legs 14 and 15, which are located on both sides of the cutout are more flexible than the wider crotch portion and can be made vertically movable in relation to one another by selecting the width of the cutout accordingly. This cutout 13 is very important for the adaptation and flexibility of the product in relation to the body. The fold in the cutout can penetrate the cleft between the buttocks of the wearer and in this way provides very good protection against leakage via the cleft between the buttocks, which type of leakage usually occurs during the use of conventional products when the wearer is lying on her back. The cutout 13 also makes it possible for said legs 14, 15 on the stiffening element to be displaced vertically in relation to one another during different body movements, for example when the wearer is walking.

In the illustrative embodiment shown in FIG. 5, the cutout 13 is wedge-shaped and located symmetrically in relation to the longitudinal symmetry line L of the product and also forms an angle β of in the order of 20°. This angle can vary within wide limits but of course depends on the design of the rear portion 2. In the case of a considerably wider design of the rear portion, such as in the design according to FIG. 5, said angle β can vary between 10° and 120°, preferably between 15° and 40°.

The stiffening element 6 also serves as the main absorption element of the product and has very great liquid-spreading capacity for rapid spreading of bodily fluid received from the wearer in the narrow crotch area directly in front of the genitals of the wearer over the absorbent portions of the whole product, that is to say over the entire stiffening and at the same time liquid-absorbing element 6. This stiffening absorbent element is designed so as to swell in the depth direction during absorption and on the whole retain its geometry in the transverse direction of the product, which results in the stiffening element retaining its fit and secure positioning in relation to the body of the wearer throughout use of the product. The absorbent stiffening element 6 has great swelling capacity in the depth direction and attendant great absorption capacity.

The stiffening absorbent element 6 consists of a fibre mat dry-formed using the method according to the invention with a density between 0.15 and 0.75 g/cm$^3$ and a weight per unit area of in the order of 200–400 g/m². The fibre mat produced is very stiff after forming and compression. The fibre mat can be used as it is or mechanically softened to the desired hardness as described above in connection with the embodiment according to FIG. 1.

The selection of compression pattern therefore makes it possible to vary the extensibility of the fibre mat. The dry-formed fibre mat can be imparted the desired reduced stiffness and the desired extensibility by virtue of the degree of compression selected and the compression pattern selected.

Furthermore, in the method according to the present invention, it is possible to pattern-compress only specific zones for the purpose of imparting to only these zones an extensibility and stiffness which are different from the rest of the stiffening absorption element. In the same way, the stiffening absorption element can be compressed over its entire extent but with different patterns in different zones. By virtue of the possibility afforded by the method according to the invention of forming a stiffening absorption element which can in a simple manner, by virtue of the pattern compression selected, be imparted the desired stiffness and the desired extension in different zones, and in which the stiffness and extension properties can be selected essentially freely in these zones, the present invention has brought about a new and previously unknown way of controlling and guiding the shaping of an absorbent product intended for taking up bodily fluids.

As mentioned above, the stiffening absorbent element 6 has great swelling capacity in the depth direction, which, when a dry-formed fibre mat as above is used, has been achieved by great compression of the fibre mat in conjunction with its production. In the dry state, the fibre mat is hard-compressed and stiff, which affords the shaped and anatomically adapted absorption element very good stability in the fitted position on the wearer and very great spreading capacity, as a result of which the total absorption capacity of the absorption element can be optimally utilized and leakage caused by local oversaturation can to a great extent be eliminated. During absorption of liquid, the absorption body swells mainly in the depth direction but the absorption element does of course swell slightly in other directions as well. When the anatomically adapted stiffening absorption element swells, further improved anatomical adaptation is in fact achieved, which contributes to the stability and flexibility of the product in relation to the body shape of the wearer when the stiffness of the absorption element decreases during absorption and attendant swelling.

So as to function in the desired manner, the stiffening element has a stiffness of in the order of 1–15 N measured according to ASTM D 4032-82. This "Circular Bend Procedure" is described in detail in EP 336 578.

Pattern formation can take place in conjunction with compression of the stiffening absorption element. Alternatively, pattern compression can take place in a separate step after smooth compression. In the method according to the invention, the fibre web can be manufactured in a continuous web as described in connection with FIG. 2 above. After pattern-compression, individual products are cut out. Pattern-compression and cutting-out of separate stiffening absorption elements can take place in a single step in a combined cutting and pattern-compression unit.

As described above, the stiffening element can also constitute the main absorption element of the product. This is particularly suitable from the point of view of production because there are fewer elements to handle than if, for example, the stiffening element and the absorption element constitute separate elements.

Manufacturing absorbent products of the type described in connection with FIGS. 5 and 6 requires a very high degree of manufacturing accuracy in the forming of the stiffening absorption element included. If manufacturing accuracy is inadequate, there is a great risk of local distortions occurring which can in turn lead to undesirable creases which may cause leakage during use of the product.

Conventional mat-forming does not meet the desired requirements for great manufacturing accuracy combined with a high manufacturing speed.

The number of mat-forming wheels is selected according to the requirements for web speed and manufacturing accuracy. If a considerable increase in productivity is required, all that is necessary is to add another mat-forming wheel.

The invention is not limited to the illustrative embodiments described above, but a large number of variations are possible within the scope of the claims below.

In connection with FIG. 4 above, an embodiment has been described, in which mat-forming in separate moulds takes place by continuous forming of the fibre web. The scope of the invention also comprises discontinuous forming in separate moulds of part layers which are formed on different mat-forming wheels and are then combined to form separate absorption bodies.

The fibre web formed according to the present invention can consist of different types of fibres or mixtures thereof, such as mechanical, thermomechanical, chemithermomechanical or chemical pulp. Mixtures containing synthetic fibres and highly absorbent fibres are also possible.

What is claimed is:

1. A method of forming a web of fibres intended for use in absorbent products by air-laying fibres, wherein separate air flows containing fibres are fed to a number n of different mat-forming wheels, wherein a separate web layer is formed on each mat-forming wheel, wherein an intended fibre web is formed by virtue of said web layers being combined downstream of the mat-forming wheels to form a common fibre web wherein the web is formed by a number n of mat-forming wheels, where n is a whole number which is at least 3 and whereby the web is imparted greater manufacturing accuracy by virtue of a manufacturing method, wherein manufacture of the fibre web takes place at a speed in excess of 400 m/min, and wherein a desired manufacturing accuracy at the web speed is achieved by selecting a sufficient number n of mat-forming wheels.

2. The method according to claim 1, wherein the fibre web is compressed in one or more step(s) after forming.

3. The method according to claim 1, wherein at least one air flow has added to it a material in the form of fibres or particles which differs from the material in one or more of the other air flows, in which way a web containing different layers is obtained.

4. The method according to claim 3, wherein the material in the form of particles or fibres consists of a highly absorbent material, and wherein this is added to said air flow together with first-mentioned fibres.

5. The method according to claim 1, wherein highly absorbent material in the form of particles or fibres is fed in between at least one pair of adjacent mat-forming wheels by application of the fibres or particles to a web layer formed upstream.

6. The method according to claim 5, wherein the web layer formed upstream is compressed before application of highly absorbent material in the form of fibres or particles.

7. The method according to claim 1, wherein the fibre web is compressed to a density of at least 200 kg/m³.

8. The method according to claim 1, wherein separate absorption bodies are formed from the fibre web, which is combined from a number of web layers and compressed, by cutting absorption bodies of a desired shape and size out of the fibre web.

9. The method according to claim 1, wherein separate web layers consist of layers which are separate in a web direction and are intended for forming separate absorption bodies, wherein the separate web layers are produced continuously on n mat-forming wheels which are provided with mat-forming moulds arranged along a periphery, wherein layers, which are separate along said periphery, for absorption bodies are formed in said mat-forming moulds and remaining fibre material on the mat-forming wheels is separated, and wherein the layers for absorption bodies are combined downstream of the mat-forming wheels to form a web of separate individual absorption bodies.

10. The method according to claim 9, wherein the separate layers are made in different sizes on different mat-forming wheels, a combined absorption body having different weight per unit area and density in different areas.

11. The method according to claim 9, wherein one or more of the web layers formed on the mat-forming wheels is or are compressed after forming.

12. The method according to claim 1, wherein a manufacturing speed of the web can be increased while retaining manufacturing accuracy in terms of variations in weight per unit area in the web formed by adding more mat-forming wheels.

13. The method according to claim 1, wherein a manufacturing accuracy in terms of variations in weight per unit area in the web formed can be increased by adding more mat-forming wheels, in which way even extremely thin fibre webs can be formed with great accuracy.

14. The method according to claim 1, wherein the combined fibre web is compressed to a stiffness in a dry state of in the order of 1–15 N measured according to ASTM D 4032-82.

15. The method according to claim 14, wherein a dry-formed fibre web is, after compression, mechanically softened to a desired hardness.

16. The method according to claim 14, wherein the dry-formed fibre web is imparted a desired reduced stiffness and a desired extensibility by a degree of compression selected and a compression pattern selected.

17. The method according to claim 16, wherein the the dry-formed fibre web is compressed with different compression patterns in different areas on those part portions of the fibre web intended for forming separate absorption cores, as a result of which the separate absorption cores produced have different flexural rigidity in said different areas.

18. The method according to claim 1, wherein the absorbent product is a sanitary napkin, incontinence product, or nappie.

19. The method according to claim 7, comprising: compressing the fibre web to a density between 300 kg/m$^3$ and 700 kg/m$^3$.

* * * * *